United States Patent [19]

Pastan et al.

[11] Patent Number: 5,458,878
[45] Date of Patent: Oct. 17, 1995

[54] P. EXOTOXIN FUSIO PROTEINS HAVE COOHG220101AL ALTERATIONS WHICH INCREASE CYTOTOXICITY

[75] Inventors: Ira Pastan, Potomac; Vijay K. Chaudhary, Rockville; David Fitzgerald, Silver Spring, all of Md.

[73] Assignee: The Government of the United States of America as represented by the Secretary of the Department of Health and Human Services, Rockville, Md.

[21] Appl. No.: 522,563

[22] Filed: May 14, 1990

Related U.S. Application Data

[63] Continuation-in-part of Ser. No. 459,635, Jan. 2, 1990, abandoned.

[51] Int. Cl.$^6$ .......................... A61K 39/104; C07K 3/00; C07K 15/28; C12P 21/08
[52] U.S. Cl. ..................... 424/260.1; 424/279.1; 435/69.7; 530/387.3; 530/391.7
[58] Field of Search .............. 424/85.91, 260.1, 424/279.1; 435/69.7; 530/387.3, 391.7

[56] References Cited

U.S. PATENT DOCUMENTS

4,545,985 10/1985 Pastan et al. ................. 424/260.1
4,892,827 1/1990 Pastan et al. ................. 435/193

OTHER PUBLICATIONS

Siegall et al., *Proc. Nat'l. Acad. Sci. USA*, vol. 85, Dec. 1988, pp. 9738–9742.
Chaudhary et al., *Nature*, 1988.
Hwang et al., *Cell*, Jan., 1987.
Chaudhary et al., *Proc. Nat'l Acad. Sci USA Genetics*, vol. 84, Jul. 1987 pp. 4538–4542.
Siegall et al; *J. of Biological Chemistry*, vol. 264, No. 24, Aug., 1989, pp. 14256–14261.
Chaudhary et al., *Proc. Nat'l. Acad Sci USA*, vol. 84, Jan. 1990, pp. 308–312.
Munro et al, *Cell*, vol. 48, Mar., 1987, pp. 899–907.
Chow et al; *J. of Biol. Chem.*, vol. 264, No. 31, Nov., 1989, pp. 18818–18823.
Waldmann, *J. of Nat'l Cancer Inst.*, vol. 81, No. 12, Jun., 1989, pp. 914–923.
Lorberboum–Galski, *Proc. Nat'l. Acad. Sci USA*, vol. 86, Feb., 1989, pp. 1008–1012.
Lorberboum–Galski, *J. of Biol. Chem.*, vol. 263, No. 35, Dec., 1988, pp. 18650–18656.
Lorberboum–Galski, *Proc. Nat'l. Acad. Sci USA*, vol. 85, Mar., 1988, pp. 1922–1926.
Bailon et al., *Biotechnology, Nov., 1988, pp. 1326–1329*.
Ogata et al., *J. of Immunology*, vol. 141, No. 12, Dec., 1988. 4224–4228.
Case et al., *Proc. Nat'l Acad. Sci USA*, vol. 86, Jan., 1989, pp. 287–291.

*Primary Examiner*—David L. Lacey
*Assistant Examiner*—T. Michael Nisbet
*Attorney, Agent, or Firm*—Townsend and Townsend and Crew

[57] ABSTRACT

A target-specific, cytotoxic, recombinant Pseudomonas exotoxin is described. Such toxins are made by inserting specific recognition molecules at specific cloning sites in at least domain III near the carboxyl terminus of the PE molecule. Various modifications of the carboxyl terminus of the PE molecule to increase cytotoxicity are set forth. Multifunctional, recombinant, cytotoxic fusion proteins containing at least two different recognition molecules are provided for killing cells expressing receptors to which the recognition molecules bind with specificity. Methods for producing novel recombinant PE molecules with specific properties are described.

29 Claims, 4 Drawing Sheets

P. EXOTOXIN FUSIO PROTEINS HAVE COOHG220101AL ALTERATIONS WHICH INCREASE CYTOTOXICITY

This a continuation in part of the application Ser. No. 07/459,635, filed Jan. 2, 1990, now abandoned.

The present invention is related generally to the making of improved recombinant immunotoxins. More particularly, the present invention is related to the construction of a recombinant Pseudomonas exotoxin (rPE) with specific cloning sites for the insertion of recognition molecules at least at the carboxyl end of the PE to achieve target-directed cytotoxicity and for the construction of recombinant multifunctional chimetic cytotoxic proteins.

BACKGROUND OF THE INVENTION

The mechanism by which protein toxins kill cells is quite complex. Many toxins bind to receptors on the surface of mammalian cells, are internalized by endocytosis, translocate to the cytosol and there exert an enzymatic activity that kills the target cell. Accordingly, these toxins have separate domains for cell binding, translocation and an enzymatic activity that Inactivates an essential cellular function. Pseudomonas exotoxin-A (PE) is a single polypeptide chain of 613 amino acids. X-ray crystallographic studies and mutational analysis of the PE molecule have shown that PE consists of three domains: an amino terminal cell receptor binding domain (Domain I); a middle translocation domain (Domain II); and a carboxyl terminal activity domain (Domain III). Domain III catalyzes the ADP ribosylation and inactivation of elongation Factor 2(EF-2) which inhibits protein synthesis and leads to cell death. Mutational analysis of Domain I has revealed that lysine$^{57}$ plays a major role in receptor binding. Similarly glutamic acid$^{553}$, Tyrosine$^{481}$ and histidine$^{426}$ have been shown to be important for ADP-ribosylation activity. Recently mutational analysis of domain II has shown that certain portions of this domain are absolutely required for the cytotoxicity of PE.

While constructing various chimetic toxins in which growth factors were fused to a form of PE (PE40) which was devoid of domain I, it was observed that the recombinant fusion proteins, made by attaching TGFα, interleukin-2 or interleukin-4 at the carboxyl end of PE40 had poor cytotoxic activity. Hence, an examination of the role of the carboxyl terminus of the PE molecule (domain III) was undertaken.

SUMMARY OF THE INVENTION

It is, therefore, an object of the present invention to determine the role of the carboxyl terminus of the PE molecule in its cytotoxic action.

It is another object of the present invention to identify specific regions at the carboxyl terminus of the PE molecule for the insertion of recognition molecules for selective killing of target cells.

It is a further object of the present invention to provide an improved, target-specific, cytotoxic recombinant PE molecule, wherein the improvement comprises the insertion of target-specific recognition molecule at least in domain III at the carboxyl terminus of the PE molecule.

A still further object of the present invention is to modify the carboxyl end of the PE to increase the potency of the chimeric toxin.

It is yet another object of the present invention to make cytotoxic PE with two recognition molecules (target ligands) wherein either the same recognition molecule is placed at two different termini, such as the amino terminus and near the carboxy terminus. for enhanced cellular binding, or two different recognition elements are inserted, one each at two different regions of the PE molecule, to enable more effective binding of the resulting PE molecule to the cell surface having two or more different entities. such as antigens, receptors and the like to which said recognition elements could bind.

It is an additional object of the present invention to provide a recombinant PE having repeat carboxyl end sequences for enhanced cytocidal activity.

An additional object of the present invention is to provide a multifunctional, recombinant cytotoxic chimetic protein for simultaneously killing cells expressing different types of receptors.

Various other objects and advantages will become evident from the following detailed description of the invention.

ABBREVIATIONS

Various abbreviations. symbols, terminologies and the like used herein are now set forth.

PE-40 means a PE molecule of about 40,000 Mr.(Hwang et al, 1987. Cell 48:129–136) having a deletion of domain I.

TGFa-PE40 means a chimeric protein wherein TGFa is the targeting or recognition molecule linked to PE-40. When the targeting agent is a different entity such as CD4 and the like, the chimeric protein is accordingly designated CD4-PE40 and the like.

When a numbering system is used, such as PE-Gly609, it means that the amino acid at position 609 in the sequence of the native PE has been replaced by glyclne. The same convention is used throughout the specification. The symbol means the deletion of amino acids following the symbol.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 demonstrates cytotoxicity of PE and PE mutants on Swiss cells. Various dilutions of PE proteins were made in PBS containing 0.2% human serum albumin and added to 1×10$^5$ Swiss 3T3 cells in 24-well plates. Sixteen hours later the cells were pulse labeled with 3H-leucine and TCA predictable cell associated radioactivity was determined as a measure of protein synthesis. The results are expressed as percent of control where no toxin was added. ●—● PE; ○—○ PEΔ613; □—□ PEΔ612,613; and Δ—Δ PEΔ611–613. All the assays were done in duplicate and repeated twice.

FIGS. 2A–2B show the results of competition for the cellular uptake of recombinant PE. Swiss 3T3 mouse cells were incubated with 400 ng $^3$H-PE (specific activity 3.5×10$^5$ DPM/μg) and increasing concentrations of purified mutant proteins for one hour at 37° C. Cell monolayers were washed and cell-associated radio-activity was determined. ●—●PE; ▲—▲PEglu57; Δ—Δ PEΔ612,613; ○—○PEΔ613; ■—■ PEgly$^{276}$; □—□ PEΔ609–613; ●—●PEΔ609–613●598–613.

FIG. 4 schematically shows the construction of a multivalent recombinant cytotoxic fusion protein using for illustration herein TGRα and anti-Tat genes. The expression plasmid pJB370548 contains a fusion gene encoding the first 50 amino acid of TGFα, the variable domain of anti-Tac light chain (VL, first 106 amino acids of anti-Tac light chain), a 14 amino acid linker, the variable anti-Tac heavy chain (VH, first 116 amino acids of heavy chain), and amino acids 253–613 of PE. AmpR, β-lactamase gene: B, BamH1; A, AvaI. Amino acids are shown as single letter codes. The gene is under the control of the bacteriophage T7 promoter linked to a Shine-Dalgarno sequence and an initiation codon.

DETAILED DESCRIPTION OF THE INVENTION

The above and various other objects and advantages of the present invention are achieved by a cytotoxic recombinant Pseudomonas exotoxin (rPE) having a recognition molecule inserted at least in domain III at the carboxyl terminus of the PE for selective killing of target cells recognized by said recognition molecule without substantial cytotoxicity to other cells not recognized by said recognition molecule, and by a rPE with modified "cytotoxic sequence" with increased cell killing activity. A multifunctional fusion protein having versatility, flexibility and efficacy for killing eel is expressing different types of receptors is provided.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "recognition molecule" as defined herein means those molecules or ligands which recognize only target cells desired to be killed. Examples of such recognition molecules are antibodies or portions thereof that can recognize the target cells, growth factors, lymphokines, cytokines, antigens, hormones and the like or combination thereof, which specifically bind to molecules on the surface of the target cells.

The term "cytotoxic sequence" as used herein means those variety of amino acid sequences at or near the carboxyl end of the PE, the presence of which is a prerequisite for the cytocidal activity of the toxin and the repeat sequences of which may determine the level of cytotoxicity. The examples of such sequences are KDEL, REDLK and the like as will become apparent from the various embodiments of the sequences discussed herein below.

The term "multivalent" cytotoxic recombinant fusion protein as used herein means that the recombinant fusion protein has at least two similar or different recognition molecules for receptors expressed on the target cells, to which either the first, the second or both recognition molecules bind with particular specificity. Of course, the multivalent fusion protein may be made with any of a variety of cytotoxic sequences described herein.

MATERIALS AND METHODS

Materials

Unless mentioned otherwise, the materials and reagents used herein were obtained from commercial sources. Polymerization Chain Reaction (PCR) kit, Gene Amp Kit, was obtained from Perkin Elmer-Cetus, Norwalk, Conn.

Mutants and Plasmid Constructions

Mutants were created by oligonucleotide directed mutagenesis using plasmid pVC45f+T as described by Jinno et al, 1988, *J. Biol. Chem.* 263, 13203–13207 and Jinno et al, 1989, *J. Biol. Chem.* 264, 15953–15959 or using polymerase chain reaction (PCR) as described below. pVC45f+T carries a PE gene under a T7 promoter and also contains a T7 transcriptional terminator and a f1 phage origin. The PE gene also contains an OmpA signal sequence which is cleaved upon secretion of PE into the perlplasm leaving a 3 amino acid (ala asn leu) extension at the amino terminus (Chaudhary et al, 1988, *Proc. Natl. Acad. Sci. USA* 85, 2989–2948). For PCR mutagenesis, two oligonucleotides and a 1.0 Kb SalI-EcoRI fragment of pVC45f÷T were employed. One oligonucleotide was the same as nucleotides 2216–2236 of the PE gene (Gray et al, 1984, *Proc. Natl. Acad. Sci. USA* 81, 2645–2649). Other oligonucleotides were complementary to the 3' end of the coding sequence PE gene, contained desired mutations and created an EcoRI site after the stop codon. Other unique restriction sites were also created without changing amino acids to identify the mutants. A 30 cycle PCR was performed with denaturation at 94° C. for 2 minutes, annealing at 55 C. for 1 min and polymerization at 72 C. for 3 min with 10 seconds extension per cycle using a gene amplification thermal cycler (Perkin Elmer Cetus). After the PCR, amplified fragment was cut with EcoRI and BamHI. it was purified using low melting point agarose. PCR fragments were ligated with a 4.5 Kb dephosphorylated EcoRI-BamHI fragment of pVC45f+T. Mutants were identified by unique restriction sites which were created during mutagenesis and finally confirmed by sequencing by Sanger's dideoxy-chain termination procedure using Sequenase (US Biochemical Corp.).

pVC4915f+T

This plasmid contains two mutations: Codon 608, CCG and 609, CGC were changed to CCC and GGG, respectively. This mutation results in glycine at 609 in place of arginine and creates a SmaI site between codons 608 and 609. This plasmid was used to clone various carboxyl terminal fragments of PE. pVC4975f+T: A 1 Kb BamHI-PstI fragment of pVC8 (Wozniak et al, 1988, *Proc. Natl. Acad. Sol. USA* 85, 8880–8884) was restricted with NarI, treated with T4 DNA polymerase to make blunt ends followed by EcoRI, and a 286 bp fragment was ligated to a 4.9 Kb dephosphorylated SmaI-EcoRI fragment of pVC4915f+T. pVC4985f+T: A 1 Kb BamHI-PstI fragment of pVC8 was restricted with HinfI, treated with T4 DNA polymerase followed by EcoRI and a 237 bp fragment was ligated to the 4.9 Kb SmaI-EcoRI fragment of pVC45f+T. pVC4995f+T: A synthetic oligonucleotide duplex VK192/193 (not shown), containing codons 598–613 of PE with a stop codon and an EcoRI compatible 3' end, was ligated to the 4.9 Kb SmaI-EcoRI fragment of pVC4915f+T. pVC4715f+T: This plasmid was created by PCR mutagenesis and contains restriction sites StuI, NdeI, SmaI, EcoRV and EcoRI within the 3' end of the PE gene and encodes amino acids RPHMPGDILK in place of PREDLK at 608 to 613. These unique sites were later used to make DNA segments encoding insertions and to attach various carboxyl terminal portions of PE.

pVC47195f+T

This was created by ligating oligonucleotide duplex VK191/192 to a 4.9 Kb EcoRV-EcoRI fragment of pVC4715f+T. The carboxyl terminus of this PE mutant contains amino acids RPHMPGDPDYASQPGKPPREDLK in place of amino acids 608–613 (PREDLK) of PE.

Plasmids for the insertion of receptor binding domains in the carboxyl end of PE Plasmid pVC4715f+T consists of DNA sequences encoding PE from amino acids 1 to 607 followed by a polylinker that contains StuI, NdeI, SmaI, EcoRV and AflII sites as well as encodes amino acids RPHMPGDILK. These sequence are under T7 promoter control and also contain Shine-Dalgarno region and signal sequence from OmpA of *E. coli*. Plasmid pVC4715/4E f+T is similar to pVC 4715 f+T, but also contains mutations in the receptor binding domain of PE (Domain I). These mutations are $Lys^{57} \rightarrow Glu$, $His^{246, 249} \rightarrow Glu$ and $Arg^{247} \rightarrow Glu$.

Plasmid pVC 47195/f+T is similar to pVC4715 f+T but contains a polylinker with StuI, NdeI, SmaI sites encoding amino acids RPHMPGI followed by the last 16 codons of PE that encode PDYASQPGKPPREDLK. Plasmid pVC47195/4Ef+T contains insertions of a cDNA encoding transforming growth factor α in the NdeI site of plasmids pVC 4715f+T and 4715/4Ef+T respectively. Plasmids pVC 47395f+T and pVC 47195/4Ef+T are derived from 47195f+T and pVC 47195/4Ef+T by inserting TGFα sequences into the NdeI site. Plasmid pVC 47355/4Ef+T was derived from pVC47395/4Ef+T by deleting 6 amino acids, inserting TGFα and following it with 10 amino acids of the PE carboxyl end.

A deposit of pVC49415f+t and pVC47355/4Ef+t has been made at the ATCC, Rockville, Md., on Dec. 28, 1989 under accession numbers 68198 and 68199, respectively. The deposit shall be viably maintained, replacing if it becomes non-viable during the life of the patent, for a period of 30 years from the date of the deposit, for for 5 years from the last date of request for a sample of the deposit, whichever is longer, and upon issuance of the patent made available to the public without restriction in accordance with the provisions of the law. The Commissioner of the Patents and Trademarks, upon request, shall have access to the deposit.

Protein Expression and Purification

Cultures of *E. coli* strain BL21 (λDE3) containing various plasmids were grown to OD650 of 0.6–0.8 and induced with 1 mM isopropyl-thiogalactoside for 90 minutes at 37° C. Periplasmic fractions were prepared as described by Chaudhary et al, supra. By virtue of having an OmpA signal sequence, more than 90% of each of the expressed toxin proteins were secreted into the periplasm. These proteins have a residual ala asn leu sequence at the amino end left behind after the processing of the OmpA signal sequence. Periplasmic fractions were assayed for ADP ribosylation activity and cytotoxicity. Later PE mutants were purified using a MonoQ anion exchange column (HR5/5) attached to a Pharmacia FPLC system. PE and mutant proteins eluted at NaCl concentrations of 0.22–0.26M. Upon SDS-PAGE the toxins were more than 90% pure. Protein concentration was measured by the Bradford assay Reagent (BioRad.Richmond. Calif.) using bovine serum albumin as a standard.

ADP Ribosylation and Cytotoxicity Assays

ADP ribosylation activity was assayed after the activation of PE and mutant proteins with 4M urea and 50 mM DTT unless otherwise stated (Collier et al, 1971, *J. Biol. Chem.* 246, 1496–1503). Cytotoxicity of PE mutants was determined by adding various dilutions of periplasmic proteins or purified proteins to $1 \times 10^5$ Swiss 3T3 cells in 24-well plates as described by Jinno et al, (1988) supra, and Jinno et al, (1989) supra. ADP-ribosylation and cytotoxic activities of recombinant PE and native PE (from Swiss Serum and Vaccine Institute, Berne, Switzerland) were indistinguishable.

Toxin Binding and Internalization

The ability of various mutant PE proteins to compete the binding of $^3$H-labelled PE on Swiss cells as well as internalization of various mutant PE derivatives as studied by immunofluorescence has been described by Jinno et al, (1989) supra.

Preparation of Target-Specific Immunotoxins

PE expression vectors with the cloning sites in the carboxyl end of PE to produce selective cytotoxic molecules are illustrated here with TGFa, a recognition molecule which recognizes only EGF receptor bearing cells. These cloning sites were used to insert TGFα near the carboxyl end of PE which produced a very active molecule that killed EGF receptor bearing cells when the insertion was followed by the last 10 amino acids of PE (Table A). The details of the procedure are now described.

RESULTS

Figure 1:
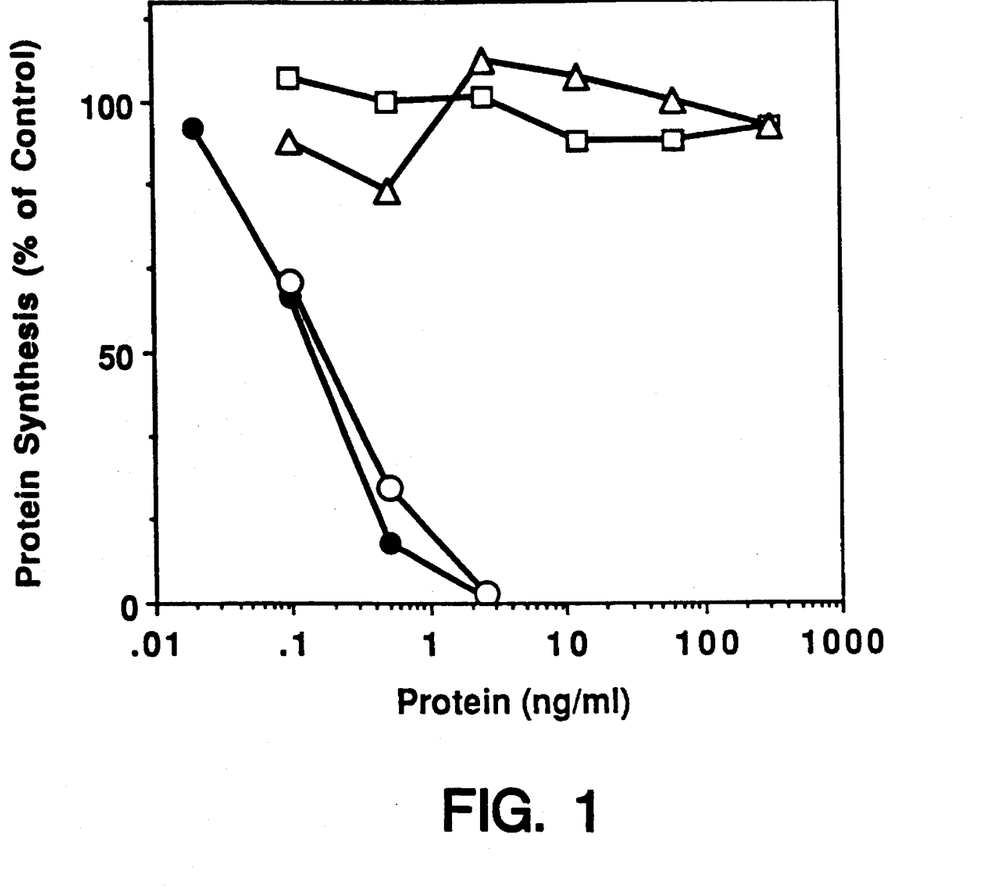

The role of sequences at the carboxyl end of PE was determined by making a series of carboxyl terminal deletion mutants that removed 1,2,3,7,8,11,14 and 24 amino acids. Removal of two or more amino acids eliminated cytotoxicity without affecting ADP ribosylation activity (Table 1, FIG. 1). In fact, even eleven amino acids (603–613) could be removed without any loss of ADP ribosylation activity. However, removal of 14 amino acids resulted in a protein with low, but measurable, ADP ribosylation activity (600–613) and removal of 24 amino acids (590–613) produced an enzymatically inactive protein. These results indicate that particular sequences at the carboxyl end of PE have a role in toxin action that are not required for ADP ribosylation activity.

The role of the carboxyl terminal sequences in toxin action was defined by creating a series of internal deletions and substitutions (Table 2). These mutations began at amino acid 602 so that ADP ribosylating activity would not be affected and extended to position 611. It was found that several small deletions encompassing amino acids 601–604 and 606–608 did not reduce cytotoxicity. Furthermore, two substitutions which altered amino acids 603–608 as well as two other substitutions within amino acids 606–608 of PE did not reduce cytotoxicity. Therefore, the sequence of amino acids in positions 602–608 did not appear to be important for cytotoxicity. However, deletions which removed arginine at 609 (pVC 49215 and pVC 49255) greatly reduced the cytotoxic action of PE. These results, together with the experiments in Table 1 showing that deletion of amino acids 612 and 613 abolish cytotoxicity, focused our attention on amino acids 609–613 which are situated at the carboxyl terminus of PE.

The role of arginine 609 was studied by either deleting it or replacing it with several different amino acids. Replacement of arginine at 609 with another basic amino acid, lysine, retained the cytotoxic activity of PE (Table 3). However, deleting arginine at 609 (pVC 49115) or replacing it with glycine, glutamic acid or leucine reduced cytotoxicity about 6–10-fold. Thus, a basic amino acid appears to be important at position 609.

To study the sequence specificity of the last five amino acids of PE, several other mutant molecules were then constructed. In two of these, the order of the acidic amino acids at positions 610 and 611 was reversed and lysine 613 deleted (Table 4, pVC 49415 and pVC 49425). These molecules were fully active whether or not position 609 was a lysine or an arginine. A molecule was also created with a leucine at position 609 and an arginine at 612 (pVC 49435) that was inactive.

Although deletion of the terminal amino acid lysine at 613 did not affect cytotoxicity, it was suspected that other mutations in this position might affect cytotoxicity in a negative manner because of the low activity of various chimetic toxins in which the ligand was placed in peptide linkage at the carboxyl terminus of PE. Therefore, lysine$^{613}$ was converted to glutamine, asparagine or aspartate. All these mutations produced a less cytotoxic molecule (Table 5). Addition of 6 or 11 amino acids to the carboxyl terminus of PE also produced a less cytotoxic molecule (data not shown). However, replacement of lys$^{613}$ with the basic amino acid, arginine, did not decrease cytotoxicity. Thus, positions 609 and 613 both require a basic amino acid for full cytotoxic activity. There are two other lysine residues at the carboxyl end of PE; these are situated at positions 590 and 606. both of these lysines could be converted to the uncharged amino acid glutamine without a decrease in cytotoxicity, indicating that a positively charged amino acid was not required at position 590 or 606 (Table 5).

Having shown the importance of particular amino acids at the carboxyl terminus of PE, it was determined that the five carboxyl terminal amino acids could be separated from the ADP ribosylation domain to regenerate an active toxin. As shown in Table 6, a fully active cytotoxic molecule could be generated from PE 609–613 (which is not cytotoxic) by the addition of amino acids 551–613, 567–613 or 598–613 of an intact PE to the carboxyl terminus of PE 609–613. Thus, the distance between the ADP ribosylation domain which ends around amino acid 600 and the essential amino acids at positions 609–613 was not critical and could be substantially increased without a decrease in cytotoxicity. Also shown in Table 6 is a PE molecule with the carboxyl terminus of RPHMPGDILK in place of PREDLK. This molecule, in which arg$^{609}$ and asp$^{611}$ were altered, was not cytotoxic. But attaching the last 16 amino acids of an intact PE molecule to give a carboxyl terminus of RPHMPGDPDYASQPGKP-PREDLK restored cytotoxicity to this molecule.

Furthermore, constructs were made in which a cDNA TGF was inserted at the carboxyl end of PE with an inactive carboxyl terminus (Table A pVC 47815/4Ef+T) and an active carboxyl terminus (Table A, pVC 47355f+T and pVC 47395f+T). The constructs with good carboxyl termini were more than 50 times as cytotoxic to cells with EGF receptors (TGFα binds to the EGF receptor) as the ones with the bad carboxyl ends. This clearly indicates that for the highest cytotoxic activity, a suitable carboxyl end is an essential requirement.

Altogether the data presented herein demonstrate that the cytotoxic activity of a PE molecule that is inactive due to a deletion or modification within the carboxyl end can be restored by attaching an intact carboxyl end. Hence, it is now possible to create active chimetic molecules by inserting a binding ligand such as TGFα at 608 within the carboxyl end of PE thus retaining the last five amino acids as REDLK.

Figure 2A:
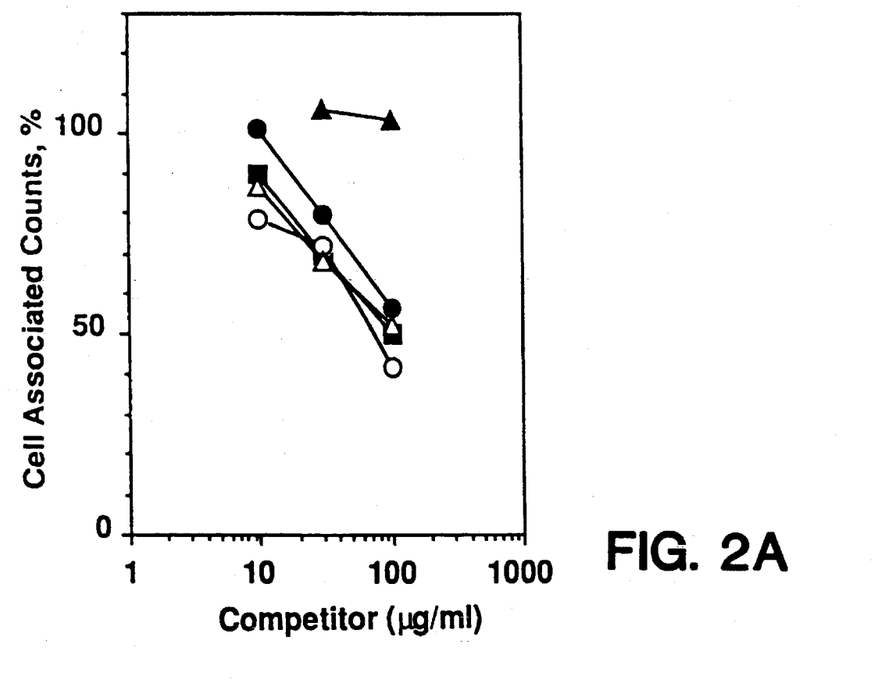
Figure 2B:
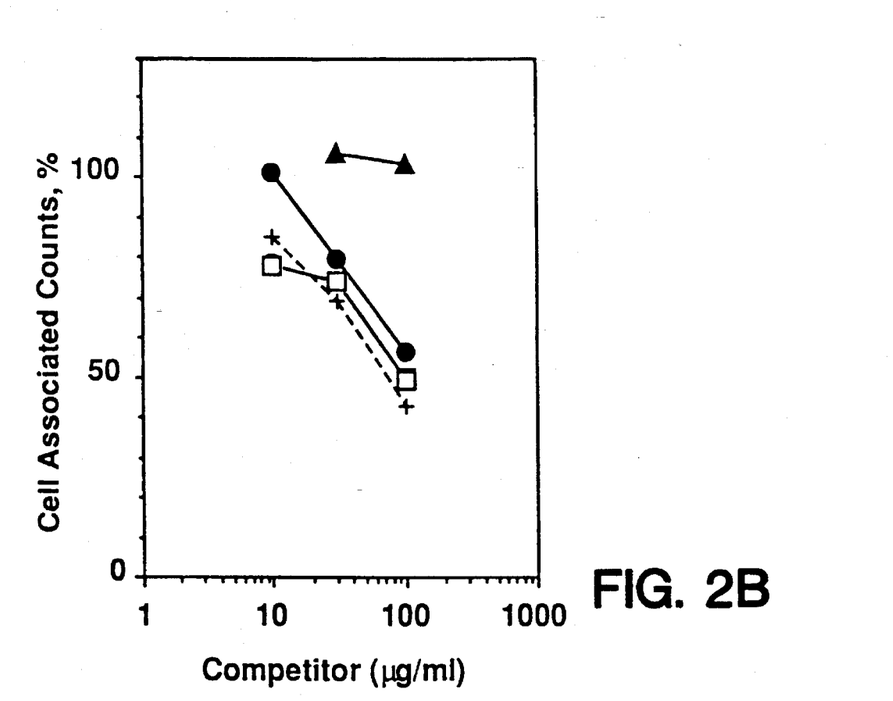
Figure 3A:
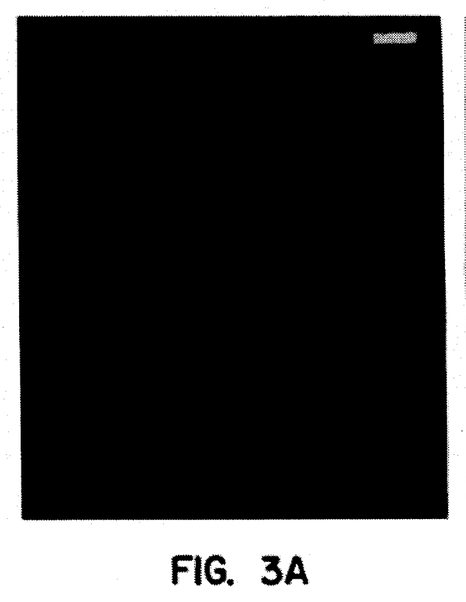
FIGS. 3A—3A show immunofluorescence detection of binding and internalization of Pseudomonas exotoxin and its recombinant variants in Swiss 3T3 cells. Swiss 3T3 cells were incubated at 37° C. for 30 minutes in the absence of toxin FIG. 3(A) or in the presence of 10 μg/ml of native Pseudomonas exotoxin (PE) FIG. 3(B), recombinant PE gly$^{57}$ FIG. 3(C) or recombinant PEΔ612,613 FIG. 3(D). Following this incubation, the cells were fixed in formaldehyde and further incubated in the continuous presence of saponin. The cells were incubated with mouse monoclonal anti PE (M40-1) (10 μg/ml), followed by affinity-purified rhodamine-labeled goat anti-mouse IgG (25 μg/ml). (Mags—×400; bar=10 μm).
Figure 3B:
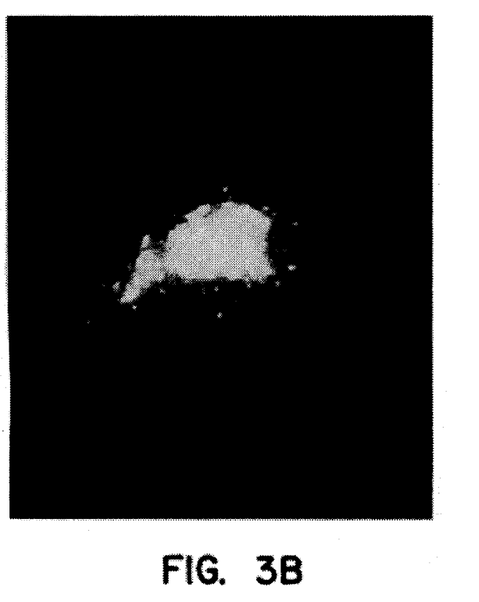
Figure 3C:
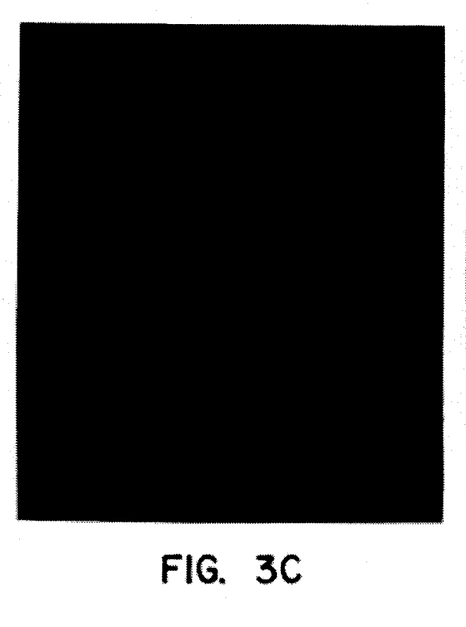
Figure 3D:
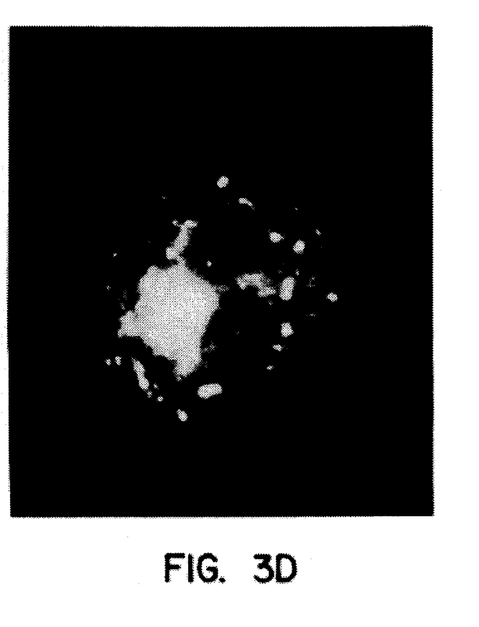

Although it has been previously demonstrated that domain I of PE is the region responsible for cell binding, it was important to show that the mutations at the carboxyl end of PE that decreased cytotoxicity did not also somehow decrease cell binding. To test this, the ability of various mutant forms of PE to compete for the uptake of [$^3$H]-PE was evaluated. As shown in FIG. 2, several PE mutants that had decreased cytotoxicity due to mutations at the carboxyl terminus of PE were just as able to compete for the uptake of [$^3$H]-PE as authentic wild type of PE. In this competition assay, PE40 which has a deletion of domain I and PEglu$^{57}$ were inactive as previously described (Jinno et al, supra).

These uptake results were confirmed using a fluorescence assay that measured the internalization of PE and various mutant PE molecules (FIG. 3). In this assay, cells are incubated with various toxins for 30 minutes to allow binding and internalization into endocytic vesicles. Molecules with a point mutation in domain I (PEglu$^{57}$) or PE40 were not internalized. In contrast, all the other PE molecules. whether or not they contained mutations at the carboxyl end of domain III, were found to have bound and internalized into endocytic vesicles and other elements in the trans-Golgi system in the perinuclear area of the cells (FIG. 3, Panel B and D). These results clearly show that decreased cytotoxicity of carboxyl terminal mutants is not due to decreased receptor binding or cellular uptake of PE molecules.

In summary, the results presented herein clearly show that mutations at the carboxyl end of PE and particularly in the last five amino acids of PE result in a molecule with full ADP ribosylation activity, but greatly reduced cytotoxicity. The data show that the amino acid sequence at the carboxyl end of PE is Arg, Glu, Asp, Leu, Lys (REDLK, Table 2). The arginine at 609 can be replaced by lysine but non basic amino acids cannot be tolerated (Table 3). Lysine at 613 is not essential and can be deleted without loss of cytotoxic activity (Table 1), but it cannot be replaced with a non-basic amino acid (Table 5). Thus, having either ArgGluAspLeu or LysGluAspLeuLys at the carboxyl terminus produced a fully cytotoxic molecule (Table 4). A search of the literature for similar sequences that were present in other molecules and performed a specific biological function revealed that the sequence which retains newly formed proteins within the endoplasmic reticulum is LysAspGluLeu (Munro et al, 1987, *Cell* 48, 899–907). Therefore, several other mutant molecules were constructed, one of which contained the exact sequence previously described as being responsible for the retention of the protein in the lumen of the endoplasmic reticulum (Table 4). It was found that a molecule ending with LysAspGluLeu (KDEL) was fully cytotoxic. Also a molecule ending in ArgAspGluLeu (RDEL) but not LeuAspGluArg (LDER) was fully active. These findings indicate that the successful entry of PE into the cytosol from an endocytic compartment requires interaction with the similar cellular component that helps retain proteins made by the cells within the endoplasmic reticulum. These findings also suggest that the sequence at the carboxyl end of PE acts as some type of recognition sequence to assist translocation of PE from an endocytic compartment into the cytosol. Other sequences that perform the same function would likewise increase the activity.

Of further significance was the finding that because the cell targeting ligands can be inserted at two cloning regions in the PE molecule (at the amino terminus as previously described or near the carboxyl end as described herein), the same or different targeting ligands can be inserted at these two regions thereby increasing either cell binding, cytotoxicity or both. Different targeting molecules at each of the two cloning regions would enable the chimetic toxin to bind to two different types of receptors present on the same cell. This is important because some antigens on target cells do not internalize well and are, therefore, poor targets for immunotoxins. But, if the chimeric toxin or immunotoxin also binds to another antigen that is well internalized, specific cell killing is increased greatly.

It was further discovered during the modificational study of the carboxyl end of the PE that if the REDLK (single letter amino acid code) sequence is replaced with KDEL, the resulting molecule is about two fold more active. Even more spectacular was the finding that a molecule with three repeats of KDEL in place of REDLK. was three times as active (Table B) indicating that by adding KDEL or equivalent repeat sequences, chimetic toxins with enhanced cytotoxicity can be produced.

In short, the present invention for the first time shows that:

1. An appropriate carboxyl end sequence is absolutely required for cytotoxicity of the PE;
2. Deletion of as few as two amino acids from the carboxyl end of PE yields a molecule that contains full ADP ribosylation and receptor binding activity, but is nontoxic to target cells (Table 1);
3. Mutational analyses indicate that PE should possess a positively charged amino acid at 609, negatively charged amino acids at 610 and 611 and a leucine at 612;
4. Lysine at 613 can be deleted but cannot be substituted with several other amino acid residues;
5. Addition of random amino acid residues at the carboxyl end of PE produce relatively inactive molecules (data not shown).
6. Addition of at least 10 carboxyl end amino acids of PE to the PE molecules that are not cytotoxic due to mutations in the carboxyl end, restores full cytotoxic activity (Table 4);
7. Different targeting ligands at different ends (amino and carboxyl) provide the flexibility of producing better binding and cytocidal PE molecules; and
8. Repeat "cytotoxic sequences" multiply the cytotoxicity in appropriate cases.

Figure 4:
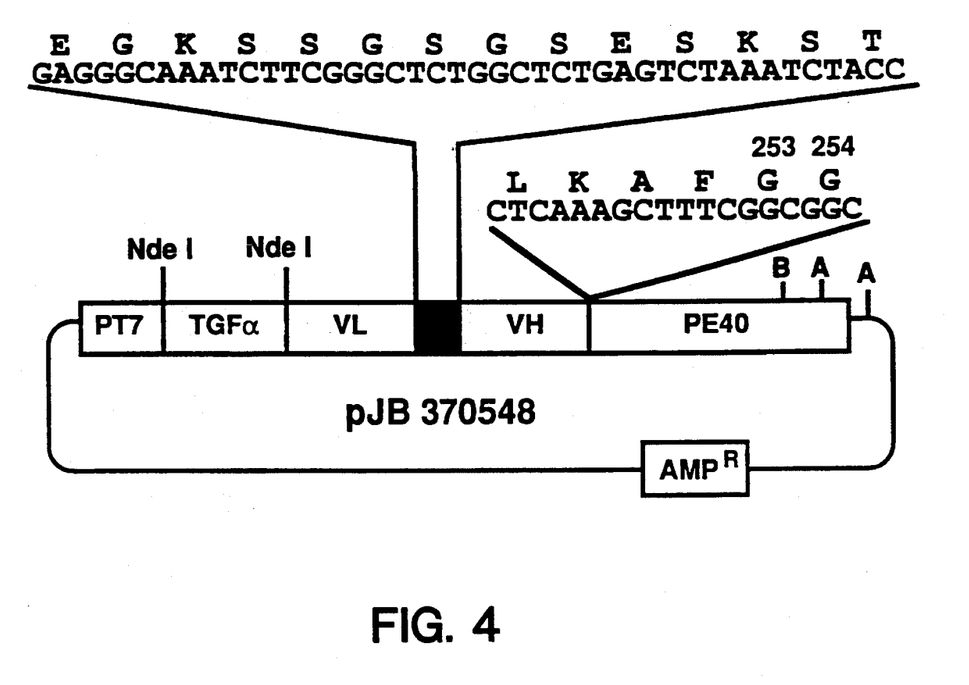

Of course, other target-specific immunotoxins are made similar to the method described herein supra by using appropriate recognition molecules, toxins and cytotoxic sequences including such modified recombinants as TGFα-PE40, CD4-PE40 and the like (See Table C). An example of a bifunctional toxin, cytotoxic for cells expressing two different receptors is now provided in accordance with the present invention to illustrate such constructions. It may be noted in this respect that conventional immunotoxins and chimetic toxins usually made in bacteria are ordinarily directed to only one receptor or antigen on target cells. The successful construction of an active chimetic toxin molecule containing more than one target recognizing entities, opens the possibility of producing chimetic molecules of greater versatility, flexibility and efficacy. FIG. 4 shows the schematic construction of pJB370548 to produce a multipurpose chimetic protein containing two recognition molecules, TGFa and anti-Tac (Fv) for binding to cells expressing either EGF, IL2 or both. Table D shows a comparison of the cytotoxic activity of this novel multifunctional recombinant fusion protein compared to monofunctional entities tested against appropriate cells easily suggested to one of ordinary skill in the art.

A deposit of pJB
370548 has been made at the ATCC. Rockville, Md., on Apr. 30, 1990 under accession number.

The deposit shall be viably maintained, replacing if it becomes non-viable during the life of the patent, for a period of 30 years from the date of the deposit, for for 5 years from the last date of request for a sample of the deposit, whichever is longer, and upon issuance of the patent made available to the public without restriction in accordance with the provisions of the law. The Commissioner of the Patents and Trademarks, upon request, shall have access to the deposit.

Of course, a method of preparing a cytotoxic, recombinant PE in accordance with the present invention, comprises the steps of utilizing the plasmid described herein without alteration or modifying said plasmid to contain a desired DNA sequence and then functionally insetting said plasmid in an expression vector so that a desired cytotoxic recombinant PE is produced and then recovering the desired PE in a substantially pure form. It is noted that the procedures for modifying, expressing and obtaining the desired PE from the plasmids are quite standard in the art and easily suggested to one of ordinary skill, given the teachings contained herein.

It is understood that the examples and embodiments described herein are for illustrative purposes only and that various changes and modifications in light thereof will be suggested to persons skilled in the art and are to be included within the spirit and purview of this application and scope of the appended claims.

TABLE 1

Deletion analysis of the carboxyl terminus of PE

| Mutants | | | |
|---|---|---|---|
| amino acids present | amino acids deleted | Cytotoxicity | ADP ribosylation activity |
| 1–589 | 590–613 | <0.1 | 0 |
| 1–599 | 600–613 | <0.1 | 20 |
| 1–602 | 603–613 | <0.1 | 100 |
| 1–605 | 606–613 | <0.1 | 100 |
| 1–606 | 607–613 | <0.1 | 100 |
| 1–610 | 611–613 | <0.1 | 100 |
| 1–611 | 612,613 | <0.1 | 100 |
| 1–612 | 613 | 100 | 100 |
| 1–613 | | 100 | |

Legend to Table 1. Mutant PE proteins were expressed in *E. coli* using T7 promoter based vector (Studier and Moffatt, 1986) and purified from the periplasm. All proteins contain a 3 amino acid (ala asn leu) extention at the amino terminus remaining after the processing of the OmpA signal sequence. These amino acids were not considered when assigning residues-numbers to the above mutant proteins. Cytotoxicity was determined by assaying inhibition of protein synthesis on Swiss 3T3 mouse cells. All results are expressed as percent of the activity obtained with recombinant full length PE molecules. All the assays were done in duplicate and at least 2 separate clones were tested.

TABLE 2

Internal deletions and substitutions within the carboxyl terminus of PE.

Location of the amino acids in PE

| Plasmid PVC | 601 | 602 | 603 | 604 | 605 | 606 | 607 | 608 | 609 | 610 | 611 | 612 | 613 | Cytotoxicity |
|---|---|---|---|---|---|---|---|---|---|---|---|---|---|---|
| 45    | A | S | Q | P | G | K | P | P | R | E | D | L | K | 100 |
| 49215 | A |   |   |   |   |   |   |   |   |   | L | K |   | <0.1 |
| 49235 | A |   |   |   | G | K | P | P | R | E | D | L | K | 100 |
| 49245 | A | S | Q | P | G |   |   |   | R | E | D | L | K | 100 |
| 49255 | A | S | Q | P | G |   |   |   |   | E | D | L | K | 0.3 |
| 4955  | A | S | Q | P | G | _P_ | _K_ | P | R | E | D | L | K | 100 |
| 4935  | A | S | _G_ | _S_ | _H_ | _L_ | _A_ | _A_ | R | E | D | L | K | 100 |
| 4955  | A | S | _E_ | _G_ | _K_ | _S_ | _S_ | _G_ | R | E | D | L | K | 100 |
| 49315 | A | S | Q | P | G | _M_ | _M_ | _M_ | R | E | D | L | K | 100 |

Mutant PE proteins were expressed in *E. coli* and purified from the periplasm. ADP ribosylation activities of all the mutants were indistinguishable from the full length PE.
Amino acids within the carboxyl end of PE (601–613) are shown as single letter code. The substitutions have been underlined.

TABLE 3

Mutations at position 609 of PE

| Plasmid (pVC) | Mutant Proteins | Cytotoxicity (% of PE) |
|---|---|---|
| 49115 | PEΔ609     | 12 |
| 49125 | PELys$^{609}$ | 100 |
| 4915  | PEgly$^{609}$ | 10 |
| 49135 | PEglu$^{609}$ | 16 |
| 49155 | PEleu$^{609}$ | 15 |

Mutant PE proteins were expressed in *E. coli* and purified form the periplasm. Substitutions are shown as replacement amino acids (also see Tables 1 and 2).

TABLE 4

Sequence specificity of last 5 amino acids of PE

| Plasmids (PVC) | 609 | 610 | 611 | 612 | 613 | Cytotoxicity (% of PE) |
|---|---|---|---|---|---|---|
| 45    | R | E | D | L | K | 100 |
| 49125 | K | E | D | L | K | 100 |
| 4215  | R | E | D | L |   | 100 |
| 49415 | K | D | E | L |   | 100 |
| 49425 | R | D | E | L |   | 100 |
| 49435 | L | D | E | R |   | <0.03 |

For details see legend to Tables 1 and 2.

TABLE 5

Mutations of the lysines residues 590, 606 and 613 in the carboxyl terminal domain of PE

| Mutants | Cytotoxicity (% of PE) | ADP-ribosylation (% of PE) |
|---|---|---|
| PEΔ$^{613}$               | 100 | 100 |
| PEarg$^{613}$             | 100 | 100 |
| PEgln$^{613}$             | 1   | 100 |
| PEglu$^{613}$             | 1   | 100 |
| PEasn$^{613}$             | 1   | 100 |
| PEgln$^{606}$             | 100 | 100 |
| PEgln$^{590}$             | 100 | 100 |
| PEgln$^{590,606,613}$     | 1   | 100 |
| PEgln$^{590,606}$arg$^{613}$ | 100 | 100 |

Analyses were performed as described in Tables I and 2.

TABLE 6

Addition of various portions of PE carboxyl terminus to PEΔ609–613

| Plasmid (pVC) | Mutant Proteins | Cytotoxicity (% of PE) | ADP-ribosylation activity (% of PE) |
|---|---|---|---|
| 4905  | PEΔ609–613                       | <0.1 | 100 |
| 4975  | PEΔ609–613+551–613               | 100  | 100 |
| 4985  | PPΔ609–613+567–613               | 100  | 100 |
| 4995  | PEΔ609–613+598–613               | 100  | 100 |
| 4715  | PEΔ609–613 RPHMPGLILK            | <0.1 | 100 |
| 47195 | PEΔ608–613 RPHMPGD+598–613       | 50   | 100 |

Legend to Table 6. A plasmid pVC4915 with a SmaI site between codons 608 and 609 of PE was created and various portions of the carboxyl terminus were attached after codon 608. pVC4995 was constructed using synthetic oligonucleotides. The last 16 amino acids (598–613) of PE consists of PDYASQPGKPPREDLK (also see Table 1 and 2). Δ means the deletion of amino acids following the symbol.

TABLE A

Cytotoxic activity on A431 cells of various carboxy terminal insertions of TGFα into PE.

| Plasmid | Protein[a] | ID$_{50}$(ng/ml)[b] |
|---|---|---|
| pVC47315/ 4E(f+)T | PE 1–607 RPHMA (TGFα) AHMPGDILK | >25 |
| pVC47395/ 4E(f+)T | PE 1–607 RPHMA (TGFα) AHMPGIPDYASOPGKPPREDLK | 0.5 |
| pVC47355/ 4E(f+)T | PE 1–607 RPHMA (TGFα) AHMPGKPPREDLK | 0.5 |

[a]Fusion proteins were partially purified from periplasm. SDS-PAGE indicated that the fusion proteins were 20–30% pure. Residues normally present in PE are underlined.
[b]ID$_{50}$ is the concentration of fusion protein (estimated as total protein concentration) that is required to inhibit protein synthesis by 50 percent as compared to control where no toxin was added. Protein synthesis was measured by 3H-leucine incorporation.

TABLE B

| Cytotoxic activity on Swiss 3T3 cells of various PE derivatives | | |
|---|---|---|
| Plasmid | Protein[a] | $ID_{50}$ (ng/ml) |
| pVC 45f+T | PE 1–608 REDLK | 1.6 |
| pVC 49415f+T | PE 1–608 KDEL | 0.76 |
| pSS 49445f+T | PE 1–608 KDELKDELKDEL | 0.55 |

[a]PE proteins were purified on Mono Q column and were approximately 90% pure.
[b]Same as Table A.

TABLE C

I. ACTIVITY OF TFGα-PE40 AND KDEL DERIVATIVES ($ID_{50}$) ON CELLS WITH EFG RECEPTORS.

| | A431 ng/ml | KB ng/ml | OVCAR 3 ng/ml | HUT 102 ng/ml |
|---|---|---|---|---|
| TGFa-PE40 | .35<br>.44 | .96 | 5.4 | >312 |
| TGFa-PE40 KDEL* | .048<br>.034 | .37 | .84 | >312 |
| TGF4-PE40 $(KDEL)_3$** | .076<br>.022 | .12 | 1.1 | >312 |

*TGFa-PE40 (253–609 KDEL)
**TGFa-PE40 (253–609 KDEL KDEL KDEL)
This TABLE shows that replacing the last 5 amino acids of TGFα-PE40 with KDEL or $(KDEL)_3$ increases its activity 3 to 10-fold.

II. CYTOTOXICITY OF CD4-PE40 DERIVATIVES ON ENV-5 CELLS THAT EXPRESS gp120 OF HUMAN IMMUNODEFICIENCY VIRUS.

| PROTEIN | $ID_{50}$ (ng/ml) |
|---|---|
| CD4-PE40+REDLK | 2.5 |
| CD4-PE40+KDEL | 0.5 |
| CD4-PE40+$(KDEL)_3$ | 0.65 |

Increased cytotoxicity of CD4-PE40 on target cells expressing HIV gp120 produced by replacing the last 5 amino acids of CD4-PE40 with KDEL or $(KDEL)_3$. ENV-5 cells express gp120.

TABLE D

Comparison of cytotoxic activity of bifunctional and monofunctional recombinant fusion proteins.

| | $ID_{50}$[a] (ng/ml) | |
|---|---|---|
| | HUT102 | A431 |
| TGFα-anti-Tac(Fv)-PE40 | 7.8 | 12.0 |
| Anti-Tac(Fv)-PE40 | 2.3 | ~500 |
| TGFα-PE40 | >500 | 0.5 |

[a]$ID_{50}$ is the concentration of the fusion protein that gave 50% inhibition of protein synthesis.

What is claimed is:

1. A fusion protein comprising a recombinant Pseudomonas exotoxin (PE) molecule, a first recognition moiety for binding a target cell, and a carboxyl terminal sequence of 4 to 16 residues which permits translocation of said fusion protein into the target cell cytosol, the first recognition moiety being inserted in domain III of PE after residue 600 and before residue 613.

2. The fusion protein of claim 1, wherein the carboxyl terminal sequence comprises, in a direction from the amino terminus to the carboxyl terminus, the following amino acid residues:

$$R^1—R^2—R^3—R^4—(R^5)_n$$

wherein, $R^1$ is a positively charged amino acid residue;

$R^2$ is a negatively charged amino acid residue;

$R^3$ is a negatively charged amino acid residue;

$R^4$ is L; and $R^5$ is a positively charged amino acid residue;

and wherein n is zero or 1.

3. The fusion protein of claim 2, wherein $R^1$ is selected from the group consisting of R and K.

4. The fusion protein of claim 2, wherein $R^2$ is selected from the group consisting of E and D.

5. The fusion protein of claim 2, wherein $R^3$ is selected from the group consisting of D and E.

6. The fusion protein of claim 2, wherein n is 1 and $R^5$ is selected from the group consisting of K and R.

7. The fusion protein of claim 2, wherein the carboxyl terminal sequence is selected from the group consisting of REDLK, KEDLK, REDLR, REDL, and KDEL.

8. The fusion protein of claim 2, wherein the carboxyl terminal sequence is KDELKDELKDEL.

9. The fusion protein of claim 2, wherein the first recognition molecule is an antibody or a portion of an antibody which recognizes the target cell.

10. The fusion protein of claim 2, wherein the first recognition molecule is selected from the group consisting of a growth factor, lymphokine, cytokine, and a hormone.

11. The fusion protein of claim 2, wherein the first recognition molecule is TGFα or CD4.

12. The fusion protein of claim 2, wherein the first recognition molecule is inserted after residue 607 of the PE molecule.

13. The fusion protein of claim 2, wherein a second recognition molecule is inserted in the toxin molecule.

14. The fusion protein of claim 13, wherein the second recognition molecule is different from the first recognition molecule.

15. The fusion protein of claim 13, wherein the second recognition molecule is anti-Tac (Fv).

16. The fusion protein of claim 13, wherein the recombinant PE molecule is TGFα-anti-Tac(Fv)-PE40.

17. A pharmaceutical composition comprising a pharmaceutically acceptable carrier and a fusion protein comprising a recombinant Pseudomonas exotoxin (PE) molecule, a first recognition moiety for binding a target cell, and a carboxyl terminal sequence of 4 to 16 residues which permits translocation of said fusion protein into the target cell cytosol, the first recognition moiety being inserted in domain III of PE after residue 600 and before residue 613.

18. The composition of claim 17, wherein the carboxyl terminal sequence comprises, in a direction from the amino terminus to the carboxyl terminus, the following amino acid residues:

$$R^1—R^2—R^3—R^4—(R^5)_n$$

wherein, $R^1$ is a positively charged amino acid residue;

$R^2$ is a negatively charged amino acid residue;

$R^3$ is a negatively charged amino acid residue;

$R^4$ is L; and $R^5$ is a positively charged amino acid residue;

and wherein n is zero or 1.

19. The composition of claim 17, wherein the carboxyl terminal residues are selected from the group consisting of REDLK, KEDLK, REDLR, REDL, and KDEL.

20. The fusion protein of claim 7 wherein the carboxyl terminal sequence is REDLK.

21. The fusion protein of claim 7 wherein the carboxyl terminal sequence is KEDLK.

22. The fusion protein of claim 7 wherein the carboxyl terminal sequence is REDLR.

23. The fusion protein of claim 7 wherein the carboxyl terminal sequence is REDL.

24. The fusion protein of claim 7 wherein the carboxyl terminal sequence is KDEL.

25. The fusion protein of claim 19 wherein the carboxyl terminal sequence is REDLK.

26. The composition of claim 19 wherein the carboxyl terminal sequence is KEDLK.

27. The composition of claim 19 wherein the carboxyl terminal sequence is REDLR.

28. The composition of claim 19 wherein the carboxyl terminal sequence is REDL.

29. The fusion protein of claim 19 wherein the carboxyl terminal sequence is KDEL.

* * * * *